United States Patent
Di Mino et al.

[11] Patent Number: 5,954,763
[45] Date of Patent: Sep. 21, 1999

[54] CORONA DISCHARGE BEAM TREATMENT OF NEURO-CEREBRAL DISORDERS

[76] Inventors: Alfonso Di Mino, 15 Arcadia Rd.;
Andre Di Mino, 159 Glen Rd., both of Woodcliff Lake, N.J. 07675

[21] Appl. No.: 08/929,015

[22] Filed: Sep. 15, 1997

[51] Int. Cl.[6] ............................................. A61N 1/02
[52] U.S. Cl. ......................... 607/154; 607/72; 607/150; 607/101
[58] Field of Search ................... 607/145, 150, 607/151, 154, 155, 72, 73, 96, 98, 99, 101, 109; 600/10, 13, 14

[56] References Cited

U.S. PATENT DOCUMENTS

| | | |
|---|---|---|
| 3,676,633 | 7/1972 | Di Mino et al. |
| 4,572,194 | 2/1986 | Head . |
| 4,667,677 | 5/1987 | Di Mino et al. |
| 5,186,171 | 2/1993 | Kuhry ..................................... 128/421 |
| 5,249,575 | 10/1993 | Di Mino et al. ........................ 607/150 |
| 5,317,155 | 5/1994 | King ........................................ 250/324 |
| 5,676,695 | 10/1997 | Di Mino et al. ........................ 607/154 |

*Primary Examiner*—Jeffrey R. Jastrzab
*Attorney, Agent, or Firm*—Michael Ebert

[57] ABSTRACT

A non-invasive therapeutic technique for treating neuro-cerebral disorders that are characterized by internal lesions, such as multiple sclerosis. In this technique, directed toward an external site on the body of the subject to be treated adjacent the internal lesions is a pulsatory corona discharge beam which scans the site and bombards the lesions with ions for a period sufficient to alleviate the disorder. The beam is produced by an energy-generating unit in which a radio-frequency carrier is modulated by an audio frequency signal that is cyclically chopped into pulses which in the course of each cycle having a one minute duration, the pulses have a progressively stepped up repetition rate, resulting in corresponding bursts of radio-frequency energy. The bursts of energy yielded by the unit are applied to the discharge electrode of an applicator from which the corona discharge beam is projected.

10 Claims, 2 Drawing Sheets

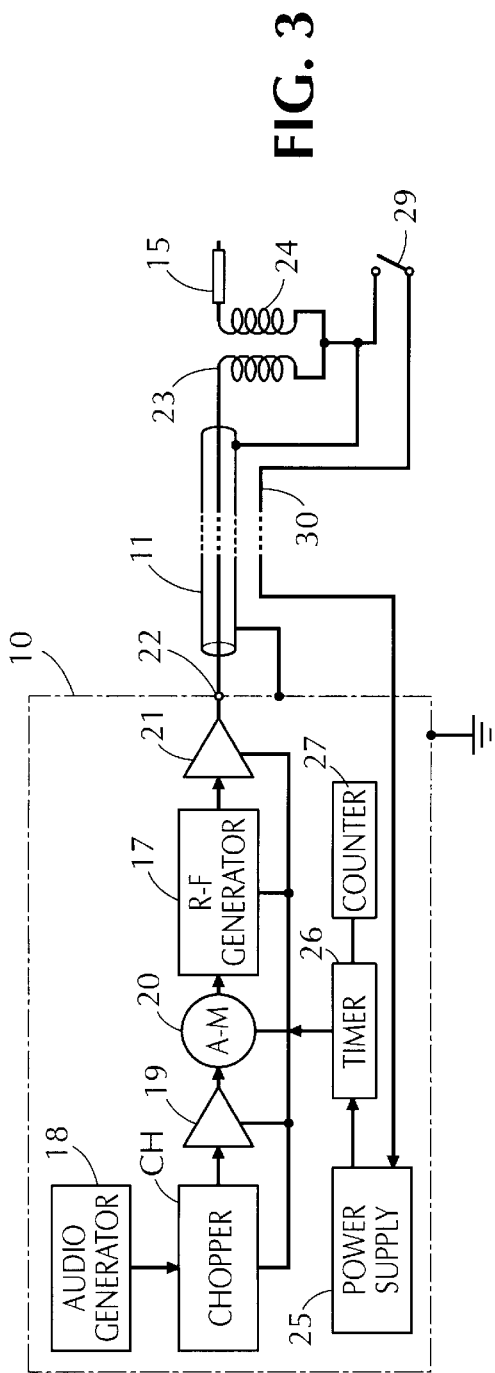
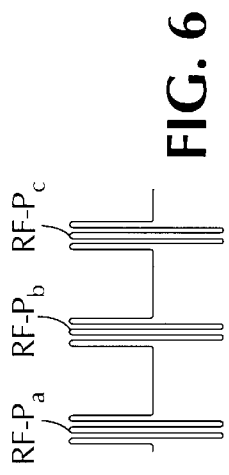
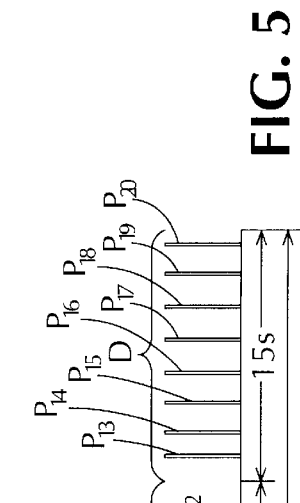
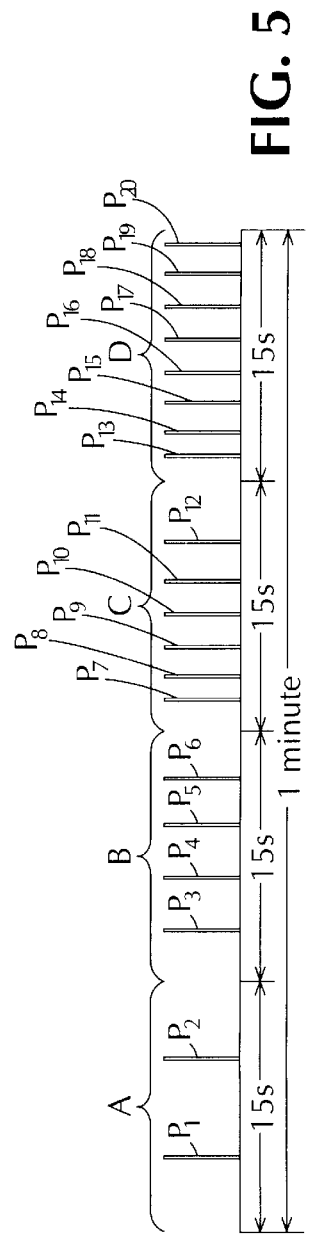

CORONA DISCHARGE BEAM TREATMENT OF NEURO-CEREBRAL DISORDERS

BACKGROUND OF INVENTION

1. Field of Invention

This invention relates generally to the treatment of neuro-cerebral disorders characterized by lesions, such as multiple sclerosis, and more particularly to a non-invasive treatment in which the lesions are subjected to a corona discharge beam which bombards the lesions with ions for a period sufficient to alleviate the disorder.

2. Status of Prior Art

The human brain is the supervisory center of the nervous system in which sensory nerve cells feed information to the brain from every region of the body, internal and external. The brain evaluates this incoming data and then sends directives through motor nerve cells to the muscles and glands to cause them to take appropriate actions. Thus if you touch a hot stove with a finger, the brain is informed of this fact by sensory nerve cells in the finger, and the brain then instructs motor nerve cells to pull the finger away from the stove.

Anatomically, the brain has three parts, the first being the hind brain which includes the cerebellum and the brain stem. The second part is the midbrain, and the third, the forebrain. The forebrain includes the cerebrum which is by far the largest sector of the brain and occupies the top most portion of the skull.

The cerebrum is split vertically into left and right hemispheres, the left hemisphere controlling the right side of the body and the right hemisphere the left side. The basal ganglia in each cerebrum hemisphere handles coordination as well as habitual but acquired skills.

The upper surface of the cerebrum is the cerebral cortex which incorporates the master controls of the body. It is in the cerebral cortex where incoming sensory data is analyzed and where motor impulses are originated to initiate, reinforce or inhibit muscle and gland activity.

It is well known that various neurological disorders are characterized by lesions in particular parts of the cerebrum (See: Principles of Neurology—Adams & Victor, 3rd Edition, McGraw-Hill—Chapter 21).

Thus the clinical manifestations of multiple sclerosis (MS) are determined by the location and extent of the foci of demyelination, the destruction of the myelin sheath of the nerve fibers. In the pathologic findings of MS, the brain and the spinal cord associated with the brain reveal numerous scattered lesions. These stand out from the surrounding white tissue in that the loss of myelin results in a pink-gray color.

The frontal lobes of the brain constitute about 30 percent of the cerebrum. Of the various effects of frontal lobe lesions, most is known about motor abnormalities caused thereby, such as spastic paralysis. Those abnormalities in motor functions which are referred to as cerebral palsy are characterized pathologically by cerebral lesions. These lesions can be identified by CT scans and ultrasound imaging. Cerebral lesions are also exhibited in Parkinson's disease which results in tremulous involuntary motion and lessened muscular power.

In a non-invasive therapeutic technique in accordance with the invention for treating neuro-cerebral disorders, the lesions which characterize these diseases are subjected to ionic bombardment by a pulsatory corona discharge beam projected from an applicator. Hence of prior art interest are applicants' prior patents which disclose corona discharge beam applicators for other purposes.

The Di Mino patents, U.S. Pat. Nos. 3,676,633 and 3,617,684 disclose a technique for changing the value of microelectronic resistors formed in a substrate. To bring about a decrease in resistance value, the surface of the resistor is subjected to a corona discharge beam. This beam is produced by radio-frequency energy which is amplitude-modulated by an audio frequency signal to generate bursts of energy which are applied to a discharge electrode from which the corona discharge beam is projected.

A luminous corona discharge is brought about as a result of the ionization of air surrounding an electrode. This phenomenon occurs when the potential gradient exceeds a certain value, but is not sufficient to cause breakdown of the air which results in sparking. When the luminous corona discharge extends from a point on the electrode to a surface spaced from this point, then the discharge is in the form of a beam rather than a halo.

Of greater prior art interest are the patents to Di Mino U.S. Pat. Nos. 4,667,677 and 5,249,575 which disclose a corona discharge technique for therapeutically treating human and animal subjects. In this technique, a corona-discharge beam is projected from an electrode toward an external site on the body being treated overlying a problem region. This beam serves to relieve pain and to gain other salutary effects, such as to alleviate an arthritic condition.

The system disclosed in Di Mino patent U.S. Pat. No. 5,249,575 includes an energy-generating unit in which a radio-frequency carrier is overmodulated by an audio-frequency signal to produce periodic bursts of radio-frequency energy whose repetition rate corresponds to the audio frequency of the signal. The output of this unit is fed by a flexible coaxial cable to a tank circuit tuned to the carrier frequency and housed within the barrel of a portable applicator gun on whose grip is mounted a trigger switch operatively connected to the unit.

Supported within the barrel and coupled to the tank circuit is a discharge electrode whose tip is adjacent the mouth of the barrel. When an operator holding the gun actuates the trigger switch, the unit is turned on and a corona discharge beam is then projected from the electrode tip, the operator positioning the gun to direct the beam toward the skin surface to be treated.

Though a system of the type disclosed in the Di Mino '575 patent is useful in relieving pain or in realizing other therapeutic effects, the corona discharge beam produced by this system is not effective to a significant degree in the treatment of neuro-cerebral disorders.

SUMMARY OF INVENTION

In view of the foregoing, the main object of this invention is to provide a non-invasive technique for treating neuro-cerebral disorders by means of a pulsatory corona discharge beam.

More particularly, an object of this invention is to provide a technique of the above type in which the lesions which characterize the disorder being treated are subjected to ionic bombardment by the pulsatory corona discharge beam.

Also an object of this invention is to provide a system for carrying out this therapeutic technique, which system includes an energy generating unit producing bursts of R-F energy having a cyclically varying repetition rate that are applied to the pulsatory discharge electrode of an applicator from which the corona discharge beam projects.

Briefly stated, these objects are attained by a non-invasive therapeutic technique for treating neuro-cerebral disorders that are characterized by internal lesions, such as multiple sclerosis. In this technique, directed toward an external site on the body of the subject to be treated adjacent the internal lesions is a pulsatory corona discharge beam which scans the site and bombards the lesions with ions for a period sufficient to alleviate the disorder.

The beam is produced by an energy-generating unit in which a radio-frequency carrier is modulated by an audio frequency signal that is cyclically chopped into pulses which in the course of each cycle having a one minute duration, the pulses have a progressively stepped up repetition rate, resulting in corresponding bursts of radio-frequency energy. The bursts of energy yielded by the unit are applied to the discharge electrode of an applicator from which the corona discharge beam is projected.

BRIEF DESCRIPTION OF DRAWING

For a better understanding of the invention reference is made to the attached drawing wherein:

FIG. 3 is a block diagram showing the various stages of the energy-generating unit included in the system and the applicator gun connected to the output of the unit;

FIG. 4 is a section taken through the barrel of the gun;

FIG. 5 shows the pulses produced by chopping the audio signal which modulates the radio frequency carrier produced in the energy-generating unit; and FIG. 6 illustrates the pulsatory radio-frequency carrier applied to the discharge electrode.

DETAILED DESCRIPTION OF INVENTION

Figure 1:
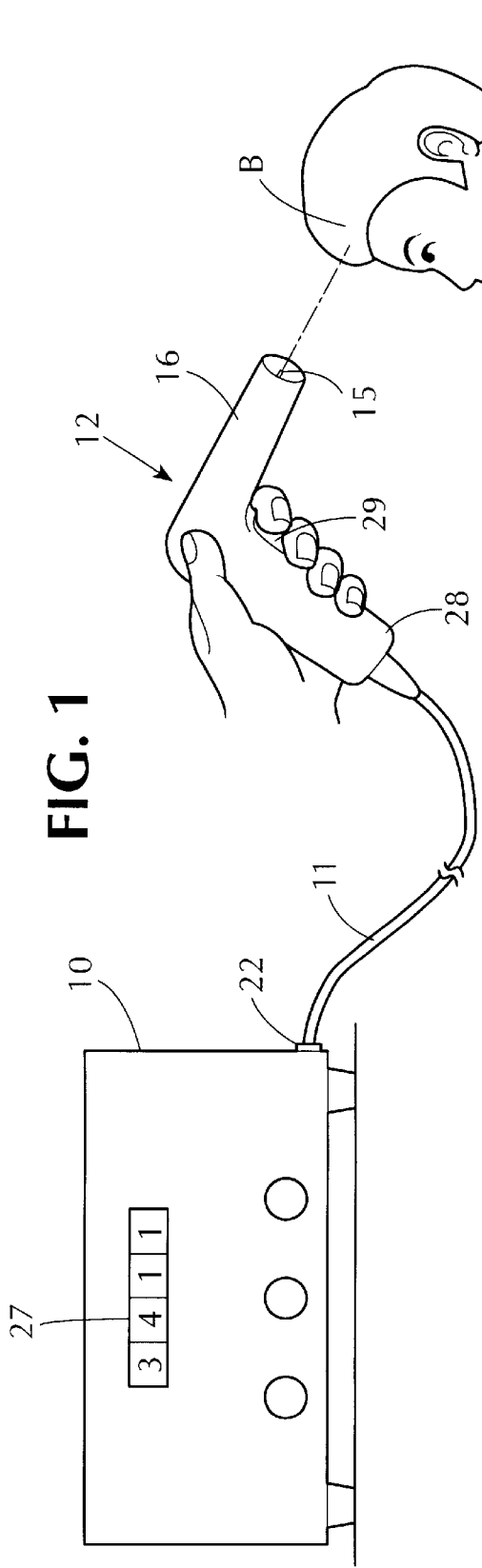
FIG. 1 illustrates the basic components of a corona-discharge beam system in accordance with the invention for treating neuro-cerebral disorders.

The Basic System:

Referring now to FIG. 1 showing a system in accordance with the invention, included in this system is an energy-generating unit 10 in which a radio frequency carrier is modulated by an audio frequency signal. This signal is chopped into pulses which cyclically, in the course of each minute, have a progressively stepped repetition rate. This results in corresponding bursts of radio-frequency energy which are applied to a discharge electrode from which is projected a pulsatory corona-discharge beam.

The bursts of radiao-frequency energy yielded by unit 10 are fed by a flexible cable 11 to a hand-held applicator gun 12 within whose barrel 16 is mounted a discharge electrode 16 from which the corona-discharge beam B is projected.

Figure 2:
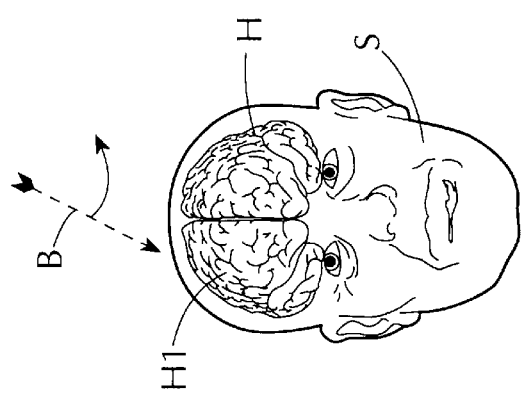
FIG. 2 shows the direction of the corona-discharge beam with respect to the cerebrum of the brain of a subject being treated.

Beam B is directed toward an external site on the body of a subject S suffering from a neuro-cerebral disorder, such as multiple sclerosis, characterized by lesions, the site on which beam B impinges, being adjacent these lesions. Thus, as shown in FIG. 2, beam B may be applied to a site on the skull of subject S below which are the left and right hemispheres $H_1$ and $H_2$ of the cerebrum containing the lesions. Or the corona-discharge beam, when treating other neuro-cerebral disorders, may be projected towards a site overlying the lower ganglia, or adjacent the spinal column.

In practice, by means of a CT scan, an ultrasound instrument, or other imaging apparatus, one may locate the lesions characterizing the neuro-cerebral disorder to be treated. In this way one may focus the corona-discharge beam 12 at a site on the subject that is adjacent these lesions. And the beam B is so as to scan all areas of the site to bombard the lesions with ions for a period sufficient to reduce the visible symptoms of the disorder, and thereby alleviate the disorder.

Because the corona-discharge beam is pencil-like and impinges on a site in which the zone of engagement is small, in order to irradiate a site having a relatively large area, the beam is repeatedly scanned over this area so that the entire area is subjected to treatment.

A corona-discharge is a highly active glow region surrounding a discharge electrode. When the electrode is a pointed wire or rod as in the present case, this glow region extends a short distance beyond this point. Assuming the wire is negatively charged, the free electrons in the air in the region of the intense electric field surrounding the wire, gains energy in this field to produce positive ions and other electrons by collision. In turn, these new electrons are accelerated and produce further ionization. This cumulative process results in an electronic avalanche in which the positive ions are accelerated toward and bombard the charged wire. As a consequence of such ionic bombardment, secondary electrons are ejected from the tip of the electrode which act to sustain the corona discharge.

When the voltage applied to the discharge electrode is elevated to a level exceeding the point at which a stable corona discharge is maintained, the air dielectric then completely breaks down to cause a spark discharge. In order therefore to produce a corona discharge, the peak voltage on the discharge electrode must be relatively high but below the level resulting in a spark discharge.

The continuous application of radio-frequency energy of relatively low power to an electrode will not result in a corona discharge. But because in the energy-generating unit 10, the continuous radio-frequency energy is produced in short bursts which shock-excite a tank coil included in the unit, the resultant energy surges have a peak amplitude sufficient to produce a sustained corona discharge beam.

The Energy Generating Unit:

Referring now to FIG. 3, the energy generating unit 10 includes a radio-frequency oscillator 17 producing an R-F carrier lying in the low frequency R-F range of 200,000 to 450,000 Hz. A preferred carrier frequency is 430,000 Hz. In practice, this oscillator is frequency-controlled by a piezo-electric crystal oscillator, the R-F carrier also being stabilized as to amplitude.

Also included in the unit is an audio-frequency generator 18 operating in the audio-frequency range of 300 to 1000 Hz to produce a sonic signal. The preferred audio frequency is 420 Hz. This audio signal which is chopped into pulses by a chopper CH in a manner to be later described, is amplified in amplifier 19 and applied to an amplitude modulator 20. Modulator 20 is so connected to radio-frequency oscillator 17 as to effect amplitude modulation of the R-F carrier.

In amplitude-modulation, the amplitude of the radio-frequency carrier is varied in accordance with the audio signal, the resultant modulated wave containing side bands that are the sum and difference of the carrier and signal frequencies. If the modulation index "M" is zero, no signal information is conveyed to the carrier. When, however, M=1(100% modulation), then in the case of a sinusoidal carrier wave, the envelope of the carrier varies from zero to twice the value of its unmodulated amplitude. But if "M" exceeds unity, the carrier is then overmodulated, as a consequence of which the carrier is periodically interrupted at a repetition rate in accordance with the audio-frequency signal.

The radio frequency carrier produced by R-F oscillator 17 is overmodulated by an audio signal that is chopped into pulses, this resulting in bursts of radio-frequency energy which correspond to the chopped audio pulses. These bursts of energy from R-F oscillator 17 are applied through an output amplifier 21 to the output jack 22 of the energy-generator unit.

Plugged into output jack 22 of the energy generating unit 10 is one end of coaxial cable 11 which connects the output of the unit to the tank coil 23 of a tank circuit. The tank circuit is housed within barrel 16 of applicator gun 12, the tank coil being tuned to the carrier frequency of the unit. Tank coil 23 is inductively coupled to an output coil 24 to which is connected the discharge electrode 15. It is to be noted that the outer shielding conductor of coaxial cable 11 is grounded, the inner conductor connecting one end of the tank coil 23 to output jack 22, the other end of the tank coil and the corresponding end of the output coil being connected to the grounded conductor. Because of this arrangement, there is no radiation from the coaxial cable.

Because tank coil 23 is shock excited by the bursts of the radio-frequency energy, the resultant damped wave surges in coil 23 have a high peak amplitude, and this causes the desired corona discharge to produce a beam which is both visible and audible. The reason it is visible is that the corona beam in the region adjacent the electrode tip produces a blue glow, and the reason it is audible is that the bursts of energy are at a sonic rate and can therefore be heard. In practice, the power output of the system may be in the order of 5 to 15 watts.

Unit 10 is provided with a direct-current power supply 25 whose output is applied to the various stages of the unit through a cycle timer switch 26 so that the unit is activated only when the cycle timer switch is "on." Thus the timer switch may be set to cyclically activate the unit for a predetermined time period, say for five minutes, during which a pulsatory corona discharge beam is produced to treat a neuro-cerebral disorder, this period being followed by a shorter relaxation interval, say two minutes, during which the timer switch is turned off. The cyclical operation of the unit prevents subjecting the subject to an overdose of ions and also prevents overheating of the unit itself should the unit be kept on continuously for a prolonged period.

The cycle timer also makes it possible to meter the dosage applied to the subject; this being done by a resettable digital counter 27 coupled to the timer.

Gun 12 is provided with a grip 28 having a trigger switch 29 mounted thereon. This switch, one contact of which is grounded, is connected by a line 30 to power supply 25. In this way, the unit 10 is only turned on when an operator holding gun 12 in his hand actuates the trigger switch. In practice, the trigger switch may be arranged to actuate a relay having a time delay characteristic, so that once the trigger is momentarily pulled, the unit is turned on for, say, a 15-second interval, and does not release until this interval is completed.

The applicator gun may be shaped like a typical hair blow dryer, and it is even lighter than such a dryer, for all it contains is the tank circuit and the discharge electrode. Because the operator is free to manipulate the gun which is connected to unit 10 by a long cable (say 6 feet in length), he is able to treat any site on the subject.

The Chopper Action:

In the corona-discharge beam systems disclosed in the above-identified DiMino prior patents in which the beam applied to a human or animal subject serves to relieve pain or an arthritic condition, the corona beam is produced by applying to a discharge electrode periodic bursts of R-F energy. These bursts are produced by modulating an R-F carrier with a signal having an audio frequency. Thus if the R-F carrier has a frequency of 400,000 Hz, and the audio signal has a frequency of 300 Hz, then bursts of R-F energy having a frequency of 400,000 Hz occur at a rate of 300 bursts per second.

In a technique in accordance with the invention for treating neuro-cerebral disorders, the corona-discharge beam serves to inject ions into the lesions which characterize the disorder being treated. In order to achieve effective penetration of these ions into the lesions, it is necessary that the ions bombarding the lesions cyclically increase in volume and therefore in intensity as to flow in a wave-like manner into the lesions. This wave-like flow of ions acts to modify the cellular structure of the lesions rather than to destroy their structure.

Chopper CH chops the audio signal from audio generator 18 applied to amplitude modulator 20 into audio pulses in accordance with a predetermined cyclical pulse pattern. In practice, chopper CH may take the form of a power transistor pulse-activated by a pulse generator conrolled by a microprocessor programmed to produce the desired cyclical pulse pattern.

A preferred form of pulse pattern is one in which in the course of each minute period during which the audio signal is applied to the power transistor, the transistor is activated to chop the audio signal into audio pulses in accordance with the pattern. The nature of the pattern is such that in the course of each cycle which lasts one minute, the resultant audio pulses have a progressively stepped repetition rate.

It is these audio pulses which modulate the R-F carrier yielded by ascillator 18 and result in corresponding bursts of R-F energy that are applied to discharge electrode 15 to produce a pulsatory corona discharge beam that is effective in treating neuro-cerebral disorders.

FIG. 5 illustrates the audio pulse pattern cyclically produced by chopper CH during each minute period of the audio signal, which period is divided into four 15 seconds segments A, B, C and D. The chopper action is such that in the first 15 seconds segment A, there are produced two audio pulses $P_1$ and $P_2$ per second. Hence in the course of the 15 seconds segment A, chopper CH produces 30 pulses.

In the second 15 seconds segment B, chopper CH produces four audio pulses $P_3$, $P_4$, $P_5$ and $P_6$, per second. Hence in the course of this 15 seconds segment, chopper CH produces 60 pulses. In the third segment C, chopper CH produces six audio pulses $P_7$ to $p_{12}$, per second, thereby yielding 60 pulses in the course of this 15 seconds segment. And is the last segment C, chopper CH produces eight audio pulses $P_{13}$ to $P_{20}$, per second, thereby yielding 90 pulses in the course of this 15 seconds segment.

Therefore during each cyclical minute of operation, the bursts of R-F energy produced by the energy-generating unit 10 and applied to discharge electrode 15 correspond to the chopped audio pulses $P_1$ to $P_{20}$, and have the same progressively stepped pattern. Thus, as shown in FIG. 6 the first three R-F bursts are RF-$P_a$, RF-$P_b$ and RF-$P_c$, these being the first three pulses in the first 15 seconds segment A in which 30 pulses are produced.

The R-F energy bursts in the course of each minute period have a progressively stepped repetition rate, for in the first 15 seconds segment, the repetition rate is two pulses per second, in the second 15 seconds segment, the repetition rate is four pulses per second, in the third segment it is six pulses per second, and in the fourth segment it is eight pulses per second. The same pulse pattern is repeated in the course of the succeeding minutes of operation.

Hence in the course of each minute period of operation the volume and therefore the intensity of ions produced by the corona-discharge beam bombarding the lesions increases in progressive steps from a low to a high intensity. And since the operation is cyclical, the flow of ions toward the lesions assumes a wave-like form, which invades the cellular structure of the lesions to bring about a remedial action which ameliorates the neuro-cerebral disorder being treated.

We have found that patients having neuro-cerebral disorders characterized by lesions who are treated by a technique in accordance with the invention exhibit a significant reduction in the symptoms indicative of this disorder. Thus in treating patients suffering from Parkinson's disease, the tremors resulting from this disease were measurably reduced.

While there has been shown and described a corona-discharge beam treatment for treating neuro-cerebral disorders in accordance with the application, it will be appreciated that many changes and modifications may be made therein without, however, departing from the essential spirit thereof.

We claim:

1. A non-invasive therapeutic technique for treating a subject having a neuro-cerebral disorder characterized by internal lesions, said technique comprising the steps of:
   A. cyclically generating radio-frequency pulses which in the course of each cycle which has a fixed duration, the pulses have a progressively increasing repetition rate in an audio range to produce bursts of radio-frequency energy;
   B. applying said burst of energy to a discharge electrode from which is projected a pulsatory corona discharge beam;
   C. directing said beam to impinge on an external site on the subject adjacent the internal lesions, whereby the lesions are then bombarded with ions; and
   D. continuing to bombard the lesions with ions for a period sufficient to alleviate the disorder.

2. A technique as set forth in claim 1, in which the duration of the cycle is a one minute period.

3. A technique as set forth in claim 2, in which the minute period is divided into four 15 seconds segments, and in which the repetition rate of the pulses is increased progressively from segment to segment.

4. A technique as set forth in claim 3, in which the repetition rate of the pulses in the first segment is 2 pulses per second, in the second segment it is 4 pulses per second, in the third segment it is 6 pulses per second, and in the fourth segment it is 8 pulses per second.

5. A technique as set forth in claim 1, in which the site is adjacent the hemispheres of the cerebrum of the subject.

6. A technique as set forth in claim 1, in which the site is adjacent the spinal column of the subject.

7. A technique as set forth in claim 1, in which the site is adjacent the lower ganglion of the subject.

8. A technique as set forth in claim 1, including a preparatory step of producing an image of the lesions to determine their location, and selecting the external site so that it is adjacent the location of the lesions.

9. A system for producing a pulsatory corona-discharge beam said system including an energy-generating unit in which a radio-frequency carrier is modulated by an audio frequency signal that is cyclically chopped into pulses which in the course of each cycle the pulses have a progresively stepped up repetition rate resulting in corresponding bursts of radio-frequency energy
   said system further including an applicator gun having a barrel in which are housed a tank circuit which is connected by a cable extending from the gun to an output of the unit and a discharge electrode coupled to the tank circuit and having a tip adjacent the mouth of the barrel, from which tip is projected said beam.

10. A system as set forth in claim 9, in which the audio frequency signal is produced by an oscillator whose output is coupled to an electronic chopper to produce said pulses.

* * * * *